United States Patent [19]

Takagi et al.

[11] Patent Number: 5,682,224
[45] Date of Patent: Oct. 28, 1997

[54] OPHTHALMOLOGICAL INSTRUMENT WITH IMPROVED ALIGNMENT MECHANISM

[75] Inventors: Akinari Takagi; Hiroshi Iijima, both of Tokyo, Japan

[73] Assignee: Kabushiki Kaisha Topcon, Tokyo, Japan

[21] Appl. No.: 548,155

[22] Filed: Oct. 25, 1995

[30] Foreign Application Priority Data

Oct. 26, 1994 [JP] Japan .................................. 6-262609
Dec. 22, 1994 [JP] Japan .................................. 6-320019

[51] Int. Cl.$^6$ ............................... A61B 3/14; A61B 3/10
[52] U.S. Cl. .................... 351/208; 351/205; 351/221
[58] Field of Search ........................ 351/208, 206, 351/205, 209, 210, 211, 221, 200, 240; 128/648, 652; 384/62

[56] References Cited

U.S. PATENT DOCUMENTS

| 4,812,033 | 3/1989 | Ishikawa | 351/208 |
| 4,944,303 | 7/1990 | Katsuragi | 128/648 |

*Primary Examiner*—Hung X. Dang
*Attorney, Agent, or Firm*—Finnegan, Henderson, Farabow, Garrett & Dunner, L.L.P.

[57] ABSTRACT

An alignment luminous flux is projected toward the cornea of an eye-to-be-detected by an alignment light projecting optical system. The alignment luminous flux reflected by the cornea is imaged on two light receiving means by an alignment light imaging optical system one of which light receiving means is disposed on the front side of an light collecting position adjacent to the cornea when the cornea is in a correct working distance and the other of which is on the back side.

7 Claims, 3 Drawing Sheets under the present invention
OPHTHALMOLOGICAL INSTRUMENT WITH IMPROVED ALIGNMENT MECHANISM

BACKGROUND OF THE INVENTION

This invention relates to an ophthalmological instrument and more particularly to an ophthalmological instrument including an alignment light projecting optical system for projecting an alignment luminous flux toward the cornea of an eye to be tested, and an alignment light imaging optical system for imaging the alignment luminous flux, which has been reflected by the cornea, on light receiving means for the purpose of detecting a working distance.

There is known one such conventional ophthalmological instrument, in which a spot light is projected toward the cornea of an eye to be tested by an alignment light projecting optical system, and the alignment light luminous flux reflected by the cornea is received by light receiving means via a diaphragm disposed on a tail end portion of an optical path of the alignment light imaging optical system, so that vertical and lateral alignments of the eye and an apparatus body and a working distance between the eye and the apparatus body can be detected based on the light receiving position and received light quantity.

However, the ophthalmological instrument thus constructed has the shortcomings in that since a single reflected alignment luminous flux is detected by a single light receiving means, when the instrument is applied, for example, to a non-contact type intraocular pressure measuring instrument for which a strictly accurate alignment is required, various limitations of design occur such as an allowable range of the working distance being determined based on setting conditions of an allowable range of alignment, and in addition, the allowable ranges of alignment and working distance are varied depending on a reflectance of the cornea and especially, with respect to the working distance, different reflectance of the cornea directly affects the setting of the allowable range and as a result, the allowable range of the working distance is greatly varied.

The present invention has been accomplished in view of the above shortcomings.

SUMMARY OF THE INVENTION

It is, therefore, an object of the present invention to provide an ophthalmological instrument, in which when an allowable range of alignment has been established, a working distance can be set in a somewhat allowable range and the working distance can be detected irrespective of reflectance of the cornea of an eye to be tested.

To achieve the above object, according to the invention as defined in claim 1, there is provided an ophthalmological instrument comprising an alignment light projecting optical system for projecting an alignment luminous flux toward the cornea of an eye to be tested, and an alignment light imaging optical system for imaging the alignment luminous flux, which has been reflected by the cornea, on light receiving means in order to detect a working distance, wherein two of the light receiving means are provided, one being disposed on the front side of a position where the reflected alignment luminous flux is imaged when the cornea is in a correct working distance and the other on the back side.

In the ophthalmological instrument thus constructed, an alignment luminous flux is projected toward the cornea of the eye by the alignment light projecting optical system and the alignment luminous flux reflected by the cornea is imaged on two light receiving means one of which is disposed on the front side of a position where the reflected alignment luminous flux is imaged when the cornea is in a correct working distance and the other of which on the back side, by the alignment light imaging optical system.

DETAILED DESCRIPTION OF THE EMBODIMENT

Embodiments of an ophthalmological instrument of the present invention will now be described with reference to the accompanying drawing in which the invention is applied to a non-contact type intraocular instrument.

Figure 1:
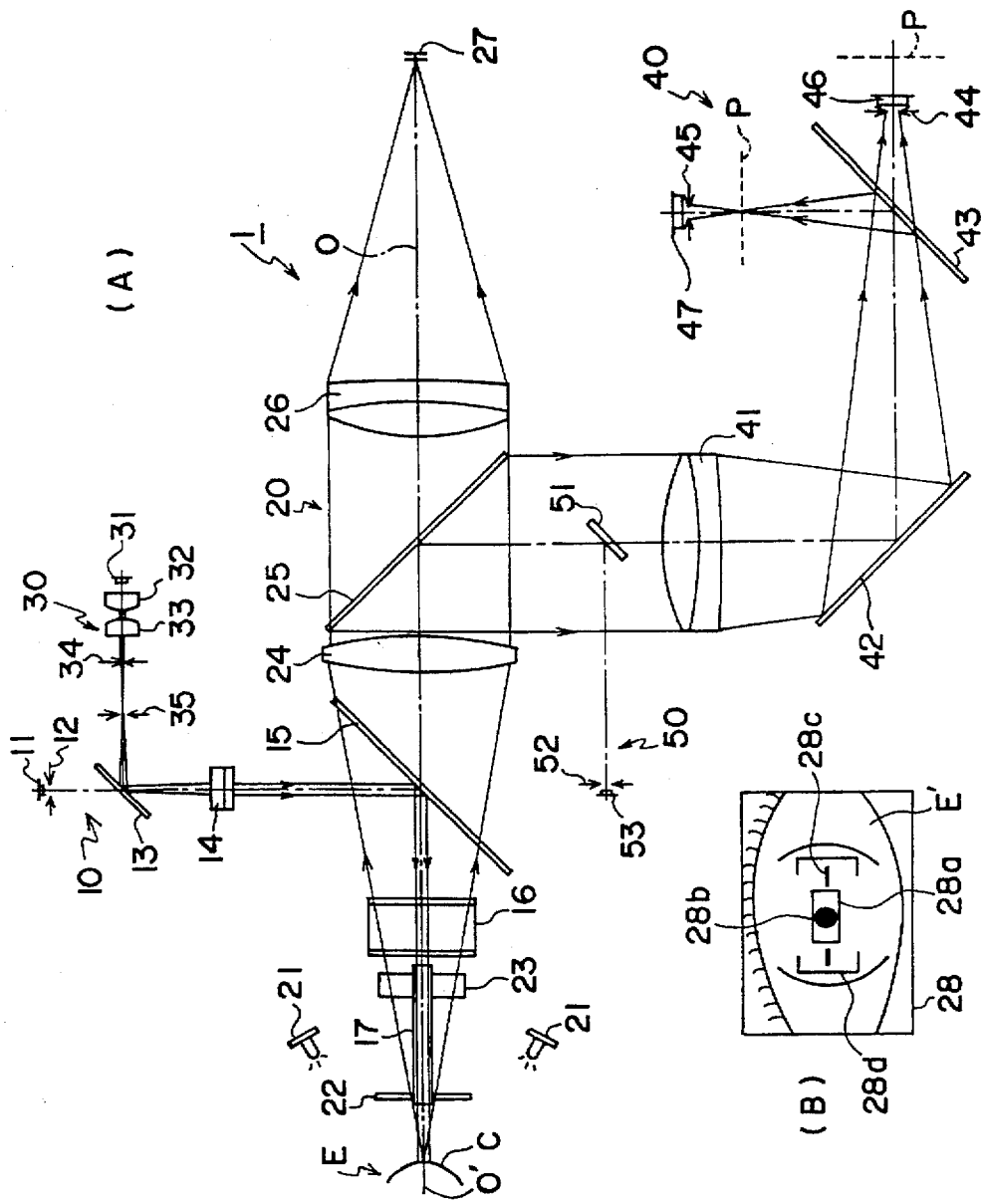
FIGS. 1(A) and 1(B) show a first embodiment of an ophthalmological instrument of the present invention and is an explanatory view of an optical system which is in detection of alignment.
Figure 2:
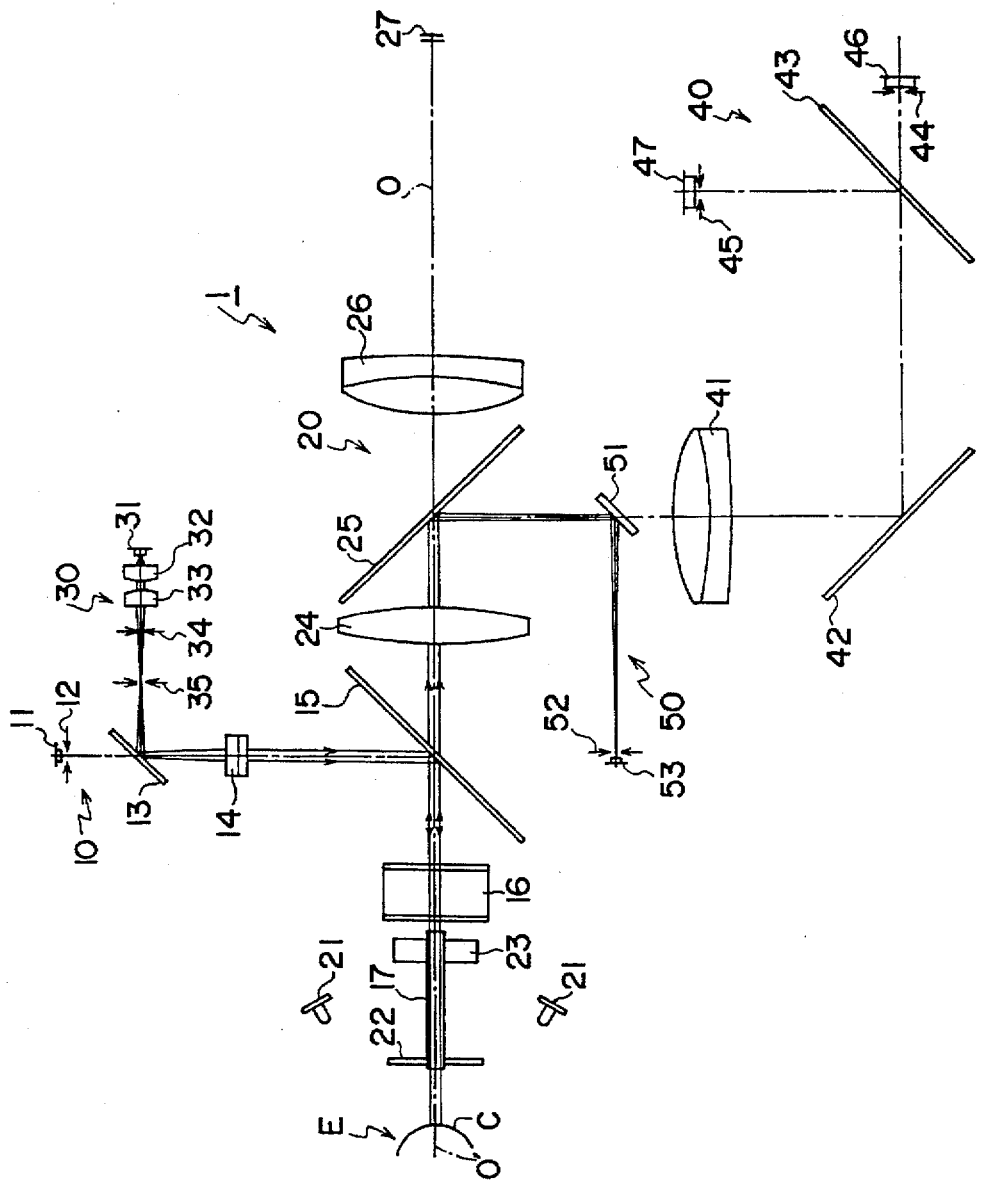
FIG. 2 is likewise an explanatory view of an optical system which is in measurement of intraocular pressure.

In FIGS. 1(A) and 2, reference numeral 10 denotes a fixation mark projecting optical system for projecting a gazing fixation mark to an eye E to be tested; 20, an antraocular portion observing optical system for observing an image of the antraocular portion including the eye E and capable of detecting an alignment (alignment detection) of an optical axis O with respect to a sight axis O' of the eye E; 30, an alignment light projecting optical system for projecting an alignment luminous flux to the eye E; 40, an alignment light imaging optical system for detecting a working distance with respect to the eye E; and 50, a corneal transfiguration detecting optical system for optically detecting a transfiguration of the cornea C, respectively.

The fixation mark projecting optical system 10 includes an LED 11 for emitting a visible light, a pin hole 12, a wavelength dividing filter 13 having the characteristic for allowing the passage of a visible light and reflecting a near infrared light, a collimator lens 14, a half mirror 15, a chamber window glass 16, and an injection nozzle 17. The chamber window glass 16 is in the form of a frame member for surrounding such a supplying device for supplying an air pulse to the injection nozzle 17, as a cylinder member.

A visible light emitted from the LED 11 and served as a gazing target passes through the pin hole 12, transmits through the wavelength dividing filter 13 and is then made into a parallel luminous flux by the collimator lens 14. After the parallel luminous flux is reflected by the half mirror 15, it is allowed to pass through the chamber window glass 16, and then through the injection nozzle 17. As a consequence, an image is exhibited to the cornea C of the eye E. The anterior portion observing optical system 20 includes a plurality of LED 21 for emitting infrared light for illuminating the eye E from the left and right sides in order to observing the anterior portion, a cover glass 22 secured to a distal end of the injection nozzle 17, a retainer glass 23 for supporting one end of the injection nozzle 17, a chamber window glass 16, a half mirror 15, an objective lens 24, a half mirror 25, an imaging lens 26, and a CCD camera 27.

The infrared light coming from the LED 21 and reflected by the eye E passes through the cover glass 22, the retainer glass 23, the chamber window glass 16, then the half mirror 15 and is then made into a parallel luminous flux by the objective lens 24. The parallel luminous flux is then allowed to pass through the half mirror 25, and collected by the imaging lens 26, so as to be imaged on the CCD camera 27.

The reflected infrared luminous flux imaged on the CCD camera 27 is input into an image processing circuit (not shown) and coded. Then, as shown in FIG. 1(B), the anterior portion image E' is displayed in a monitor screen 28. Also, in the screen 28, an alignment area 28a is displayed in an electrically combined manner.

The alignment light projecting optical system 30 includes an LED 31 for a combined use of alignment operation and intraocular pressure detection, condenser lens 32, 33, an aperture diaphragm 34, a pin hole 35 for forming an image to be projected to the cornea C, a wavelength dividing filter 13, a collimator lens 14, a half mirror 15, a chamber window glass 16, and an injection nozzle 17. The pin hole 35 is disposed at a focussing position on the back side of the condenser lens 14.

The infrared light emitted from the LED 31 passes through the condenser lens 32, 33, the aperture diaphragm 34, and the pin hole 35. The infrared light is then reflected by the wavelength dividing filter 13 and then made into a parallel luminous flux by the collimator lens 14. After reflected by the half mirror 13, the parallel luminous flux is then allowed to pass through the chamber window glass 16 and then through the injection nozzle 17. Then it is projected to the cornea C of the eye E so as to be reflected by the cornea C.

The infrared luminous flux reflected by the cornea C is caused to pass through the cover glass 22, the retainer glass 23, the chamber window glass 16, and the half mirror 15 by the anterior portion observing optical system 20. Then it is made into a parallel luminous flux by the objective lens 24 and then partly allowed to pass through the half mirror 25. After collected by the imaging lens 26, it is imaged on the CCD camera 27 and a target image 28b is displayed in the screen 28 in a combined manner.

The operator three-dimensionally moves the apparatus body so that the target image 28b is brought into the alignment area 28a. If the alignment is incorrect, the target image 28b moves upwardly and downwardly, leftwardly and rightwardly within the screen 28 and if the working distance is incorrect, a shape of the target image 28b becomes large, and a peripheral portion of the target image 28b is out of the alignment area 28a, because the target image 28b is out of focus. Thus, the operator can make an alignment and adjust the working distance by seeing this target mark.

The alignment light imaging optical system 40 commonly uses those optical parts from the cover glass 22 to the half mirror 25, and further includes an imaging lens 41, a reflecting mirror 42, a half mirror 43, diaphragms, and light receiving sensors 46, 47.

The alignment luminous flux reflected by the cornea C is reflected and partly guided to the imaging lens 41. The luminous flux thus guided to the imaging lens 41 is collected by the imaging lens 41 and reflected by the reflecting mirror 42. The reflected luminous flux is partly allowed to pass through and partly reflected by the half mirror 43. The alignment luminous flux allowed to pass through the half mirror 43 is imaged on the light receiving sensor 46 via the diaphragm 44. On the other hand, the alignment luminous flux reflected by the half mirror 43 is imaged on the light receiving sensor 47 via the diaphragm 45.

The light receiving sensors 46, 47 are disposed one on the front side and the other on the back side of a position P where the alignment luminous flux is imaged when the cornea C is in the correct working distance. In this embodiment, it is designed such that the same diaphragms 44, 45 and the same light receiving sensors 46, 47 are used. The light receiving sensors 46, 47 have calculation means, not shown, for calculating the working distance based on the ratio of the quantities of light made incident to the sensors 46, 47.

For example, if the quantity of light made incident to the light receiving sensor 46 is an $\alpha$ level and the quantity of light made incident to the light receiving sensor 47, a $\beta$ level, the light quantity ratio $\gamma$ can be expressed by the following equation.

$$\gamma = (\beta - \alpha)/(\beta + \alpha)$$

Thus, by calculating the above equation, the working distance can be obtained. The working distance is correct when $\alpha = \beta$ and $\gamma = 0$. The eye E and the apparatus body are too near when $\gamma > 0$ and too far when $\gamma < 0$. Since the correct working distance is detected by calculating the light quantity ratio, the correct working distance can be detected irrespective of the reflectance of the cornea C.

On the other hand, a working distance recognition bar 28c is displayed in the screen 28 in a combined manner based on light receiving states of the light receiving sensors 46, 47. Variation of the length of this working distance recognition bar 28c makes it possible for the operator to recognize the working distance.

For example, a working area 28d is displayed in the screen 28 in a combined manner as in the case with the alignment area 28a. A width of the working distance area 28d represents the correct working distance. If the cornea C is in the correct working distance, the length of the working distance recognition bar 28c is within the working distance area 28d, but if the cornea C is not in the correct working distance, the length of the working distance recognition bar 28c expands out of the working distance area 28d to that extent. In case the apparatus body is too close to the eye E, an indicative alarm such as "TOO CLOSE" or the like is displayed in the screen 28 so that the operator may recognize it.

On the other hand, the alignment detection by the light receiving sensors 46, 47 is made by recognizing that the quantities of light of the sensors 46, 47 are equal to or more than a predetermined level. In this case, since the light quantity ratio caused by movement of the image due to alignment on the diaphragms 44, 45 is considerably larger than the effect caused by variation of reflectance of the cornea C, the effect of reflectance of the cornea C is so small that measuring accuracy is hardly affected by it.

The corneal transfiguration detecting optical system 50 includes a reflecting mirror 51, a diaphragm 52 and a light receiving sensor 53 in addition to those optical parts from the cover glass 22 to the half mirror 25.

When the completion of alignment and adjustment of the working distance are detected by the light receiving sensors 46, 47, a signal indicative of "injection OK" is output to a air injection driving device, not shown. Upon receipt of this injection OK signal, air is injected into a space (chamber) between the retainer glass 23 and the chamber window glass 16 and the cornea C is transfigured by an air pulse injected through the injection nozzle 17. At the same time, a detection light is output toward the cornea C from the LED 21.

As shown in FIG. 2, the detection light at that time is projected to and reflected by the cornea C of the eye E via the condenser lens 32, 33, the aperture diaphragm 34, the pin hole 35, the wavelength dividing filter 13, the collimator lens 14, the half mirror 15, the chamber window glass 16, and the injection nozzle 17, as in the case with the alignment detection.

Then, the detecting light reflected by the cornea C proceeds to the half mirror 25 from the injection nozzle 17 and is reflected by the half mirror 25. The detecting light is further reflected by the reflecting mirror 51 and allowed to pass through the diaphragm 52 so as to be imaged on the light receiving sensor 53.

In the light receiving sensor 53, since the light receiving quantity of the light receiving sensor 53 is increased as soon as the transfiguration of the cornea C is started, an intraocular pressure is measured by known procedures based on a signal indicative of increase of received light quantity due to transfiguration of the cornea C. The result of calculation is displayed in the screen 28.

Next, a sequence of operation from alignment to measurement by respective optical systems will be described.

First, the LED 11 is lighted to provide a visible light to be served as a gazing mark to the cornea C of the eye E through the fixation mark projecting optical system 10, so that the person to be tested can gaze at it. Further, an infrared light emitted from the LED 31 is projected to the cornea C of the eye E by the significant light projecting optical system 30, so that the infrared light is reflected by the cornea C.

The operator observes, through the screen 28, the anterior portion image E' formed by the reflected infrared light imaged on the CCD after the infrared light coming directly from the LED 21 has been reflected by the eye E. Also, the operator manipulates the apparatus body such that the target image 28b, which is formed on the CCD 27 after being reflected by the cornea C, may be within the alignment area 28a. The operator further manipulates the apparatus body so that the working distance recognition bar 28c will be within the working distance area 28d.

The light receiving sensors 46, 47 detect the alignment by recognizing that the incident light quantities are equal to or more than a predetermined level, and further detect the working distance based on the light quantity ratio of the incoming alignment luminous flux. Upon detection of the completion of alignment and the correct working distance based on this detection result, an air pulse is injected from the injection nozzle 17 to make flat the cornea C. The detection light output toward the cornea C from the LED 31 is reflected by the flattened cornea C, and imaged on the light receiving sensor 53. The intraocular pressure is measured based on the signal indicative of increase of the received light quantity which is increased as soon as the transfiguration of the cornea C is started. The result of measurement is displayed in the screen 28.

In the above-mentioned embodiment, a reflecting mirror is used as the mirror 51 in the corneal transfiguration detecting optical system 50. In the alternative, the mirror 51 may be a half mirror so that the luminous flux passing through the injection nozzle 17 can be guided to the light receiving sensors 46, 47. In this case, even if the alignment light imaging optical system 40 has a high power, incorrect alignment can be prevented because the images on the light receiving sensors 46, 47 will not take the ring-shape having no central portion.

Also, in the above embodiment, the alignment and the working distance are detected based on the incident light quantity level to the detecting sensors 46, 47. In the alternative, an optical position detector such as a CCD camera may be disposed at the location of the diaphragms 44, 45, so that the positions and sizes of the images can be found and the alignment and the working distance can be detected based on the positions and sizes of the images. In this case, the working distance is detected based on the sizes and the ratio of light quantities of the images on the two optical position detectors.

Figure 3:
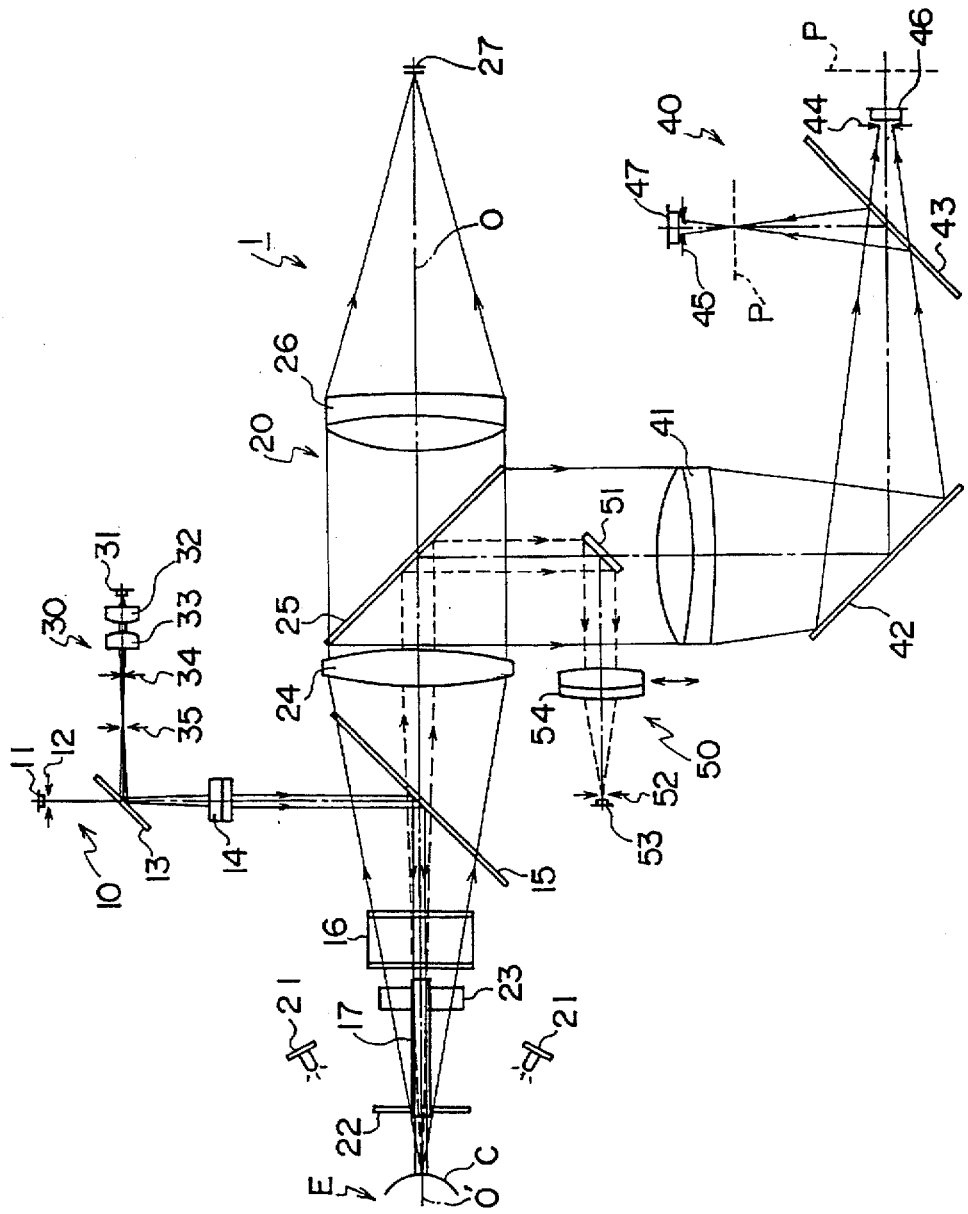
FIG. 3 shows a second embodiment of an ophthalmological instrument of the present invention and is an explanatory view of an optical system which is in detection of alignment.

As shown in FIG. 3, an imaging lens 54 may be interposed between the reflecting mirror 51 and the diaphragm 52 of the corneal transfiguration detecting optical system 50.

This imaging lens 54 is adapted to detect the alignment through the detecting sensor 53 as indicated by a chain line in the illustration. Detection of the alignment and detection of the working distance are made by separate detecting sensors 46, 47, 53, so that the degree of freedom of design is further increased and in addition, it becomes possible, for example, that stain caused by tear attached to the cover glass 22, etc. by being scattered under pressure of the air pulse injected from the injection nozzle 17 can be detected based on the ratio of light quantities of the detecting sensors 46, 47 and the detecting sensor 53 for detecting the alignment and the correct working distance and the stain can be displayed in the screen 28 for the purpose of visual recognition of the operator. When the cornea C is flattened, the imaging lens 45 is retreated from the optical path and the reflected detecting luminous flux is imaged on the light receiving sensor 53 through the above-mentioned imaging path. In FIG. 3, component parts which are identical with those of the preceding embodiment are denoted by identical reference numerals, respectively and detailed description thereof is omitted.

In this way, by displacing the locations of the detecting sensors 46, 47 on the front side and on the back side of the light collecting position, a single luminous flux is received by two light receiving means having different distances.

As a consequence, the range of the working distance can be changed even in the case where the allowable range of the alignment is established, thus enabling to increase the degree of freedom in view of design.

Since the light receiving sensors 46, 47 detect the working distance based on the ratio of light quantities of the incident alignment luminous flux, a correct working distance can be detected irrespective of the reflectance of the cornea of the eye to be tested. Thus, accuracy of detection can be further increased.

Furthermore, by displaying the relative position between the apparatus body and the cornea in the screen 28, the operability of the job for adjusting the working distance can be enhanced and in addition, an indicative alarm can be made such as "TOO CLOSE", thus enabling to further increase the safety.

Also, by virtue of a provision of a diaphragm (not shown) on the image side (this way) of the imaging lens 41, the alignment light imaging optical system 40 is telecentric to the image side.

As described in the foregoing, in the ophthalmological instrument of the present invention, two light receiving means are disposed on the front side and on the back side of the light collecting position. Accordingly, the setting of an allowable range of the working distance can have a width in the case where the allowable range of the alignment is established. Moreover, detection of the working distance is hardly affected by the reflectance of the cornea.

What is claimed is:

1. An ophthalmological instrument comprising an alignment light projecting optical system for projecting an alignment luminous flux toward the cornea of an eye to be tested, and an alignment light imaging optical system for imaging the alignment luminous flux, which has been reflected by the cornea, on light receiving means in order to detect a working distance at which an optic axis of the ophthalmological instrument coincides with a vertex of the cornea, wherein two of said light receiving means are provided, one being disposed on the front side of a position where the reflected alignment luminous flux is imaged when the cornea is in a correct working distance and the other on the back side.

2. An ophthalmological instrument according to claim 1, further comprising calculation means for calculating the working distance based on light receiving results of said front and rear light receiving means.

3. An ophthalmological instrument according to claim 1, wherein vertical and lateral alignments of the eye to be tested with an apparatus body is detected based on either one or both of the light receiving results of said front and rear light receiving means.

4. An ophthalmological instrument according to claim 1, wherein said alignment light imaging optical system is telecentric to the image side.

5. An ophthalmological instrument according to claim 2, wherein the working distance calculated by said calculation means is displayed on display means.

6. An ophthalmological instrument according to claim 2, wherein an alarm is issued by alarm means when the working distance calculated by said calculation means is equal to or less than a predetermined value.

7. An ophthalmological instrument according to claim 1, further comprising calculation means for calculating the working distance based on the ratio of the quantities of light made incident to said two light receiving means.

* * * * *